(12) United States Patent
Bradway

(10) Patent No.: US 10,709,541 B2
(45) Date of Patent: Jul. 14, 2020

(54) SYSTEMS AND METHODS FOR ADJUSTING THE DIAMETER OF AN ENDOLUMINAL PROSTHESIS AND AN ENDOLUMINAL PROSTHESIS CONFIGURED FOR THE SAME

(71) Applicant: Cook Medical Technologies LLC, Bloomington, IN (US)

(72) Inventor: Ryan C. Bradway, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 262 days.

(21) Appl. No.: 15/960,895

(22) Filed: Apr. 24, 2018

(65) Prior Publication Data

US 2018/0311030 A1 Nov. 1, 2018

Related U.S. Application Data

(60) Provisional application No. 62/491,470, filed on Apr. 28, 2017.

(51) Int. Cl.
*A61F 2/07* (2013.01)
*A61F 2/06* (2013.01)
(Continued)

(52) U.S. Cl.
CPC ............... *A61F 2/06* (2013.01); *A61F 2/07* (2013.01); *A61F 2/95* (2013.01); *A61F 2/89* (2013.01); *A61F 2/962* (2013.01); *A61F 2/966* (2013.01); *A61F 2002/067* (2013.01); *A61F 2002/9511* (2013.01); *A61F 2002/9528* (2013.01); *A61F 2002/9534* (2013.01); (Continued)

(58) Field of Classification Search
CPC ............... A61F 2/07; A61F 2002/065; A61F 2002/067; A61F 2002/072; A61F 2002/2075; A61F 2002/077; A61F 2002/9528; A61F 2002/9511; A61F 2/95
See application file for complete search history.

(56) References Cited

U.S. PATENT DOCUMENTS 4,878,906 A 11/1989 Lindemann et al.
4,913,141 A 4/1990 Hillstead
(Continued)

FOREIGN PATENT DOCUMENTS

EP 3 069 696 A1 9/2016
JP 2006-346350 12/2006
(Continued)

OTHER PUBLICATIONS

Extended European Search Report for EP Patent Application No. 18275058.8 dated Aug. 23, 2018, 8 pages.
(Continued)

*Primary Examiner* — Suba Ganesan
(74) *Attorney, Agent, or Firm* — Brinks Gilson & Lione

(57) ABSTRACT

Systems and methods of adjusting the diameter of an endoluminal prosthesis that allows for controlled radial deployment of the endoluminal prosthesis and the ability to revise the positioning of the endoluminal prosthesis after unsheathing. The endoluminal prosthesis includes a stent graft having a tubular graft wall, a stent, a main strand, a proximal strand, and a distal strand.

20 Claims, 10 Drawing Sheets

(51) Int. Cl.
*A61F 2/95* (2013.01)
*A61F 2/962* (2013.01)
*A61F 2/966* (2013.01)
*A61F 2/89* (2013.01)

(52) U.S. Cl.
CPC .............. *A61F 2002/9665* (2013.01); *A61F 2220/0075* (2013.01); *A61F 2230/001* (2013.01); *A61F 2230/0054* (2013.01); *A61F 2250/001* (2013.01)

(56) References Cited

U.S. PATENT DOCUMENTS

| | | |
|---|---|---|
| 5,693,083 A | 12/1997 | Baker et al. |
| 5,843,158 A | 12/1998 | Lenker et al. |
| 5,873,906 A | 2/1999 | Lau et al. |
| 6,346,118 B1 | 2/2002 | Baker et al. |
| 6,524,335 B1 | 2/2003 | Hartley et al. |
| 6,562,064 B1 | 5/2003 | deBeer |
| 6,692,521 B2 | 2/2004 | Pinchasik |
| 6,964,677 B2 | 11/2005 | Osypka |
| 7,160,318 B2 | 1/2007 | Greenberg et al. |
| 7,611,528 B2 | 11/2009 | Goodson, IV et al. |
| 7,803,177 B2 | 9/2010 | Hartley et al. |
| 7,909,863 B2 | 3/2011 | Hartley et al. |
| 8,043,354 B2 | 10/2011 | Greenberg et al. |
| 8,172,895 B2 | 5/2012 | Anderson et al. |
| 8,206,427 B1 | 6/2012 | Ryan et al. |
| 8,361,134 B2 | 1/2013 | Hartley et al. |
| 8,506,616 B2 | 8/2013 | Hartley et al. |
| 8,551,158 B2 | 10/2013 | Roeder et al. |
| 8,597,346 B2 | 12/2013 | Hartley et al. |
| 8,603,156 B2 | 12/2013 | Hartley et al. |
| 8,728,148 B2 | 5/2014 | Roeder et al. |
| 8,758,425 B2 | 6/2014 | Greenberg et al. |
| 8,864,808 B2 | 10/2014 | Greenberg et al. |
| 9,220,617 B2 | 12/2015 | Berra |
| 9,278,018 B2 | 3/2016 | Roeder |
| 9,622,893 B2 | 4/2017 | Huser |
| 9,855,128 B2 | 1/2018 | Kölbel et al. |
| 2001/0041925 A1 | 11/2001 | Konya et al. |
| 2002/0007208 A1 | 1/2002 | Strecker |
| 2003/0050684 A1 | 3/2003 | Abrams et al. |
| 2003/0233140 A1 | 12/2003 | Hartley et al. |
| 2004/0073289 A1 | 4/2004 | Hartley |
| 2004/0098084 A1 | 5/2004 | Hartley et al. |
| 2004/0106978 A1 | 6/2004 | Greenberg et al. |
| 2004/0138734 A1 | 7/2004 | Chobotov et al. |
| 2004/0193178 A1 | 9/2004 | Nikolchev |
| 2004/0193655 A1 | 9/2004 | Hartley et al. |
| 2004/0220655 A1 | 11/2004 | Swanson et al. |
| 2005/0085890 A1 | 4/2005 | Rasmussen et al. |
| 2005/0090887 A1 | 4/2005 | Pryor |
| 2005/0107862 A1 | 5/2005 | Ohlenschlaeger |
| 2005/0119722 A1 | 6/2005 | Styrc et al. |
| 2005/0137701 A1 | 6/2005 | Salahieh et al. |
| 2005/0288768 A1 | 12/2005 | Sowinski et al. |
| 2006/0142836 A1 | 6/2006 | Hartley et al. |
| 2006/0190070 A1 | 8/2006 | Dieck et al. |
| 2007/0100427 A1 | 5/2007 | Perouse |
| 2007/0208409 A1 | 9/2007 | Quigley |
| 2007/0233223 A1 | 10/2007 | Styrc |
| 2008/0027529 A1 | 1/2008 | Hartley et al. |
| 2008/0077226 A1 | 3/2008 | Ouellette |
| 2008/0140178 A1 | 6/2008 | Rasmussen et al. |
| 2008/0243225 A1 | 10/2008 | Satasiya |
| 2008/0294234 A1 | 11/2008 | Hartley et al. |
| 2009/0030497 A1 | 1/2009 | Metcalf et al. |
| 2009/0082842 A1 | 3/2009 | Glynn |
| 2009/0082847 A1 | 3/2009 | Zacharias et al. |
| 2009/0099640 A1 | 4/2009 | Weng |
| 2009/0112302 A1 | 4/2009 | Stafford |
| 2009/0171431 A1 | 7/2009 | Swanson et al. |
| 2009/0204202 A1 | 8/2009 | Dierking et al. |
| 2009/0259291 A1 | 10/2009 | Kolbel et al. |
| 2010/0010617 A1 | 1/2010 | Goodson, IV et al. |
| 2010/0168838 A1 | 7/2010 | Hartley et al. |
| 2010/0249896 A1 | 9/2010 | Sugimoto et al. |
| 2010/0286768 A1 | 11/2010 | Alkhatib |
| 2011/0125244 A1* | 5/2011 | Roeder .................. A61F 2/07 623/1.11 |
| 2011/0178588 A1 | 7/2011 | Haselby |
| 2011/0190865 A1 | 8/2011 | McHugo et al. |
| 2011/0230947 A1 | 9/2011 | Hartley et al. |
| 2011/0288624 A1 | 11/2011 | Roeder et al. |
| 2012/0010696 A1 | 1/2012 | Greenberg et al. |
| 2012/0172965 A1 | 7/2012 | Kratzberg et al. |
| 2012/0277848 A1 | 11/2012 | Roeder et al. |
| 2013/0116773 A1 | 5/2013 | Roeder et al. |
| 2013/0245743 A1 | 9/2013 | Norris |
| 2014/0180378 A1 | 6/2014 | Roeder |

FOREIGN PATENT DOCUMENTS

| | | |
|---|---|---|
| WO | WO 2001/74270 A2 | 10/2001 |
| WO | WO 2004/017868 A1 | 3/2004 |
| WO | WO 2004/019823 A1 | 3/2004 |
| WO | WO 2006/037086 A1 | 4/2006 |
| WO | WO 2009/126227 A2 | 10/2009 |

OTHER PUBLICATIONS

Verhoeven, et al., "The Great Registry" Lessons Learned from Real-World Experience with the GORE® C3® Delivery System, Supplement to Endovascular Today Sponsored by Gore & Associates, Feb. 2013, 6 pages.

* cited by examiner

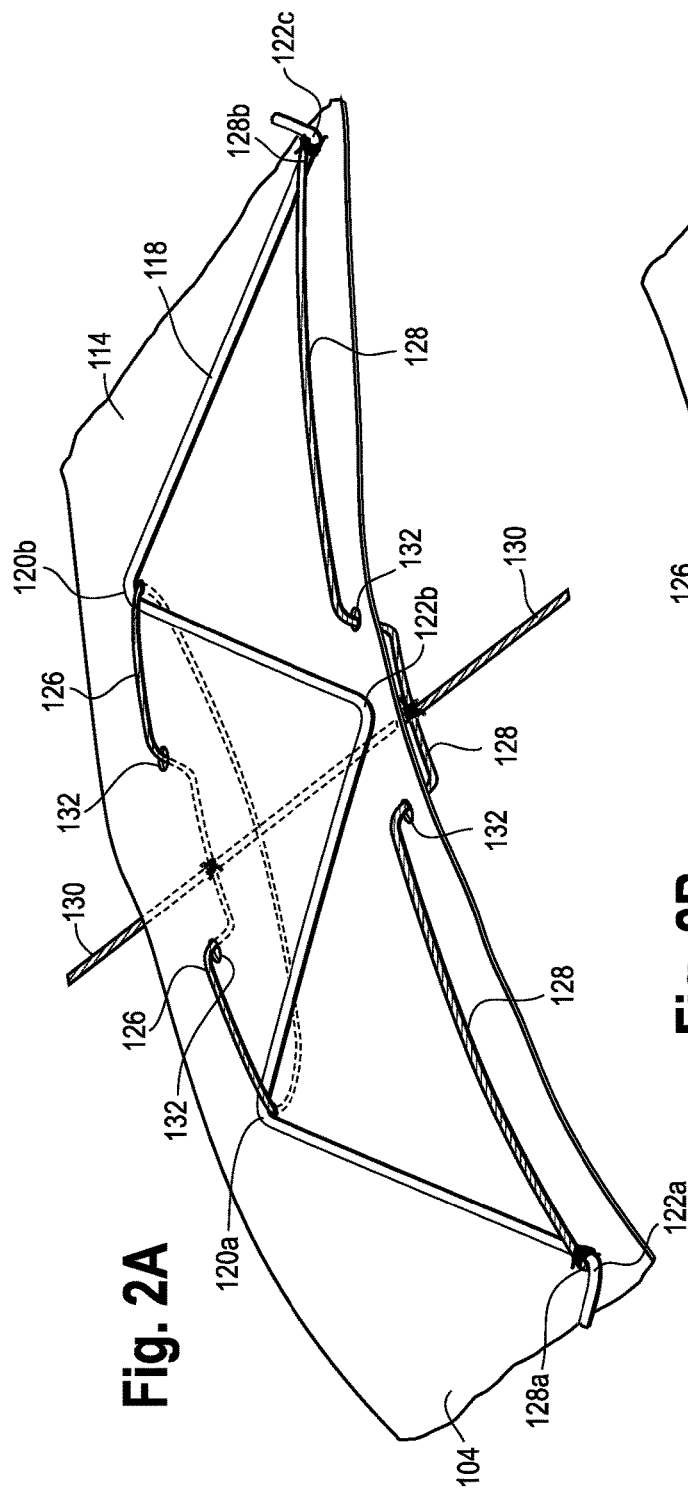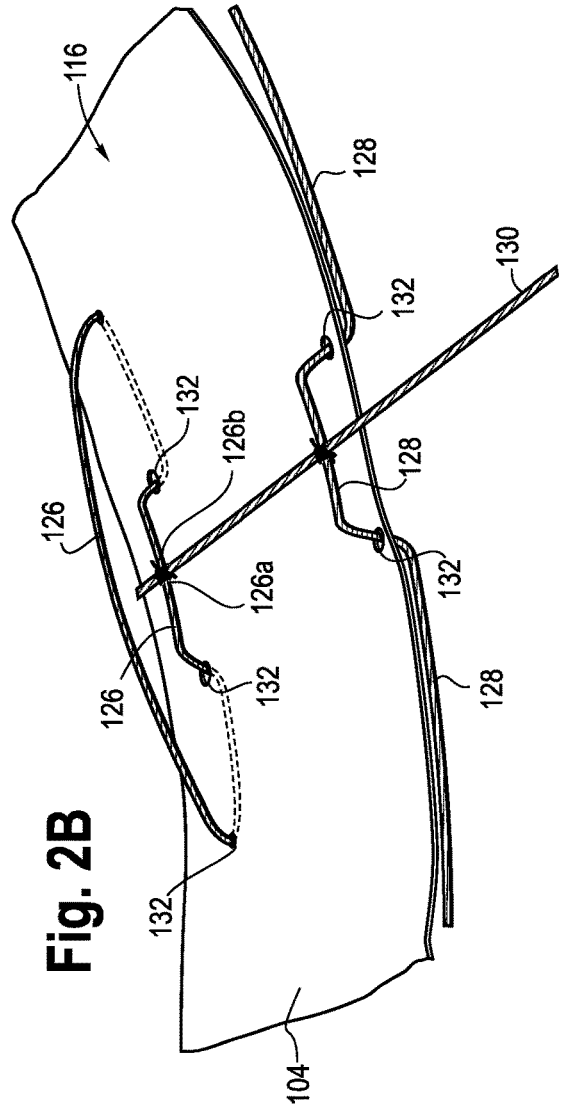

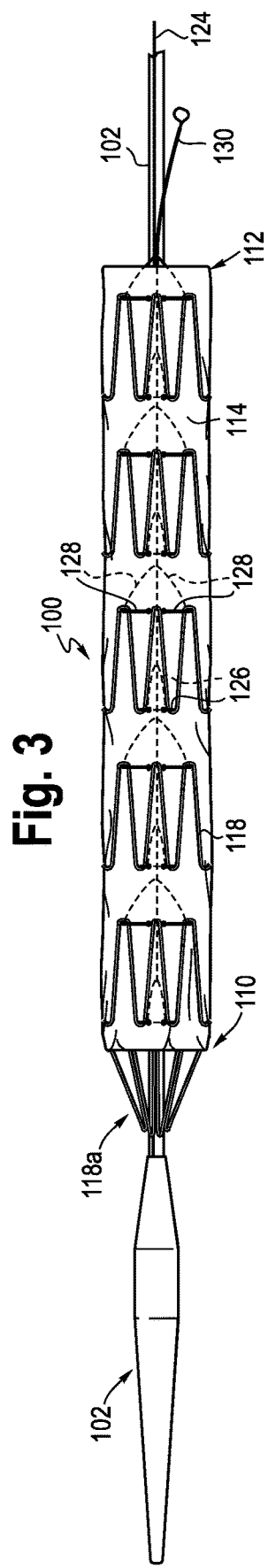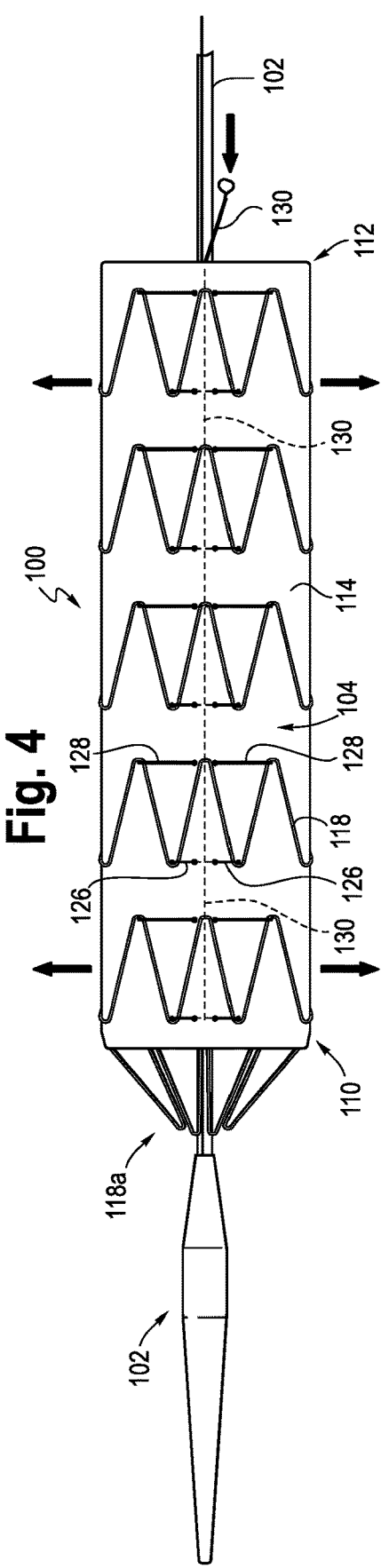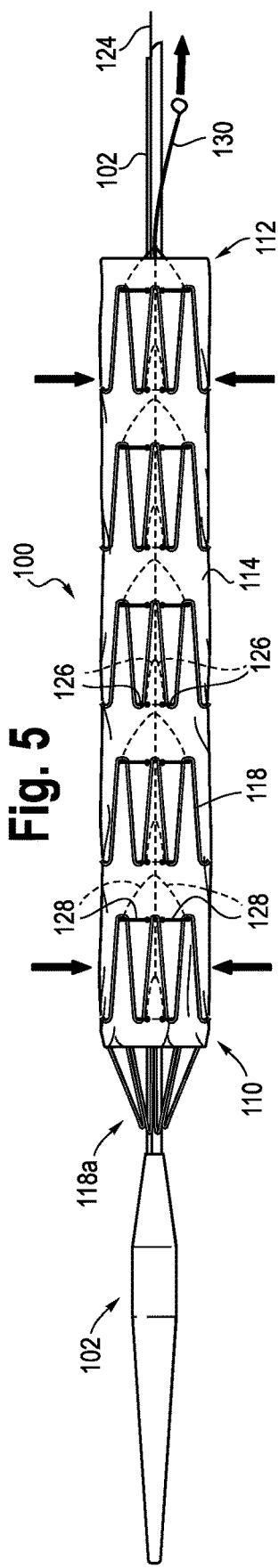

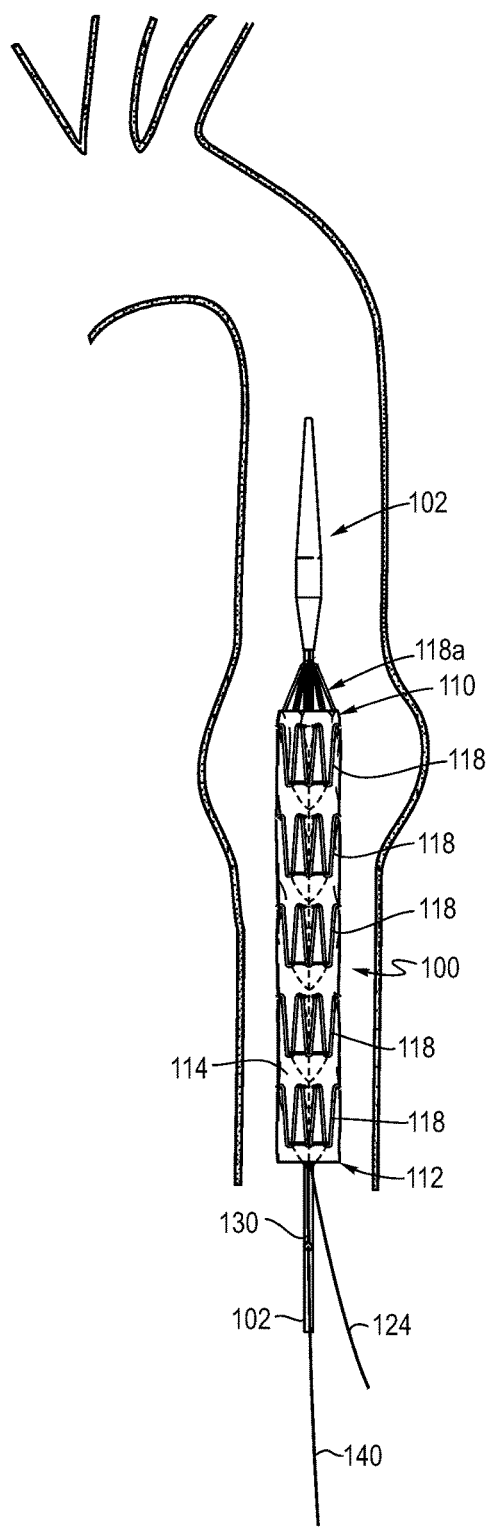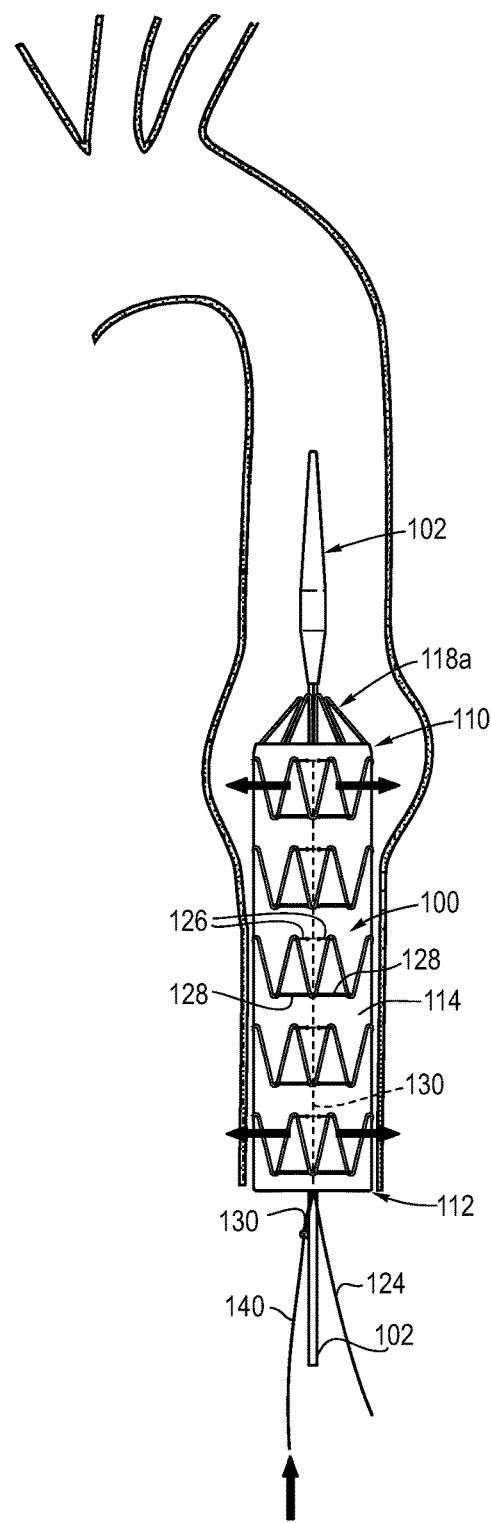

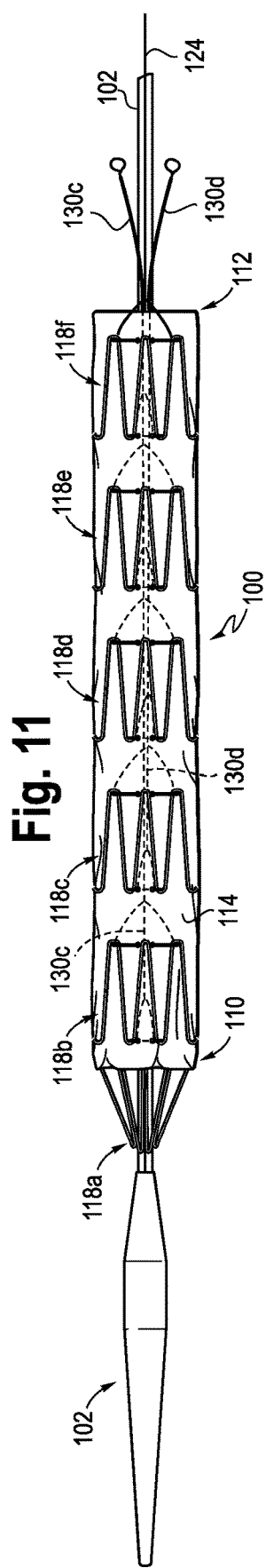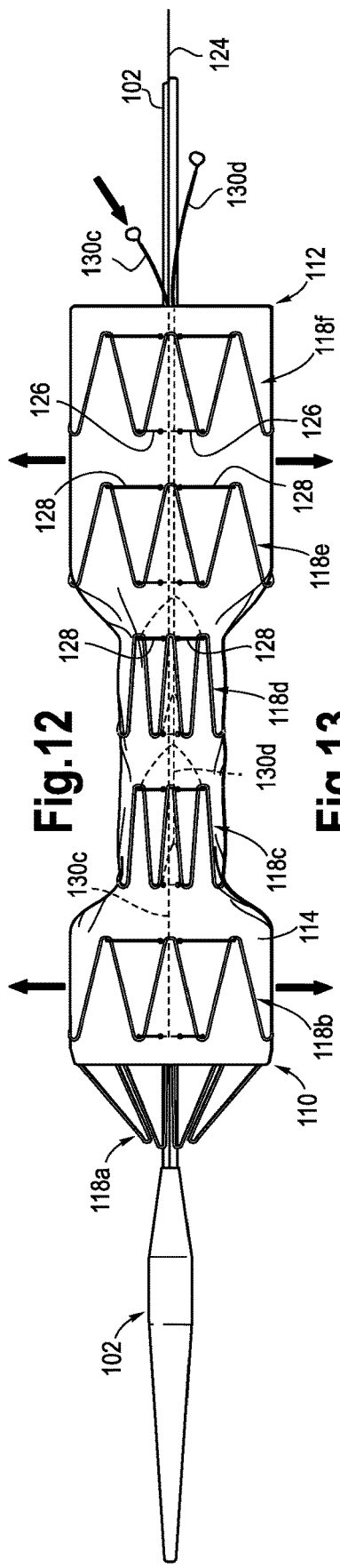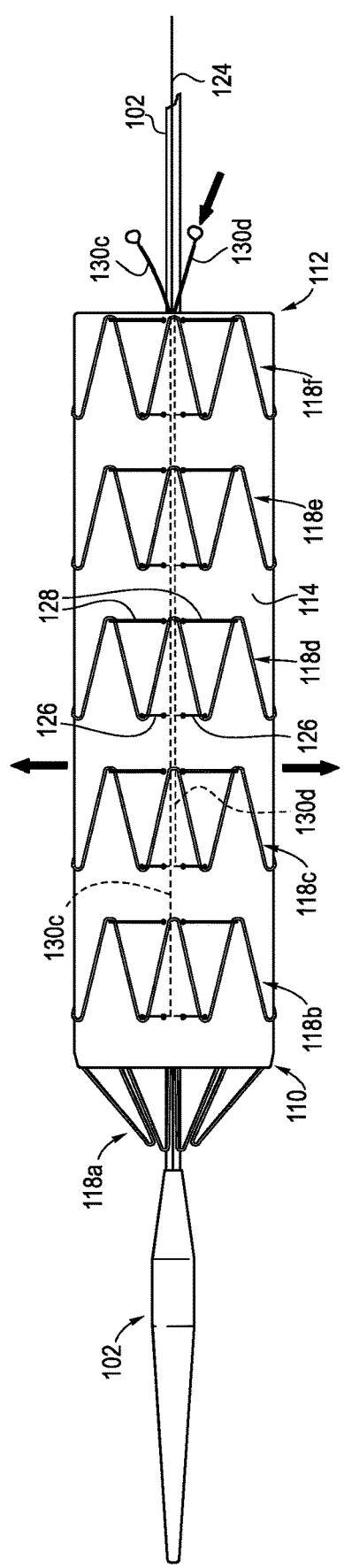

SYSTEMS AND METHODS FOR ADJUSTING THE DIAMETER OF AN ENDOLUMINAL PROSTHESIS AND AN ENDOLUMINAL PROSTHESIS CONFIGURED FOR THE SAME

RELATED APPLICATIONS

The present patent document claims priority to and the benefit of the filing date under 35 U.S.C. § 119(e) to U.S. Provisional Patent Application Ser. No. 62/491,470, which was filed on Apr. 28, 2017, and is hereby incorporated by reference in its entirety.

BACKGROUND

1. Technical Field Text

The present invention relates to systems and methods of adjusting a diameter of an endoluminal prosthesis, such as for aortic stent grafts, and an endoluminal prosthesis configured for the same.

2. Background Information

Endovascular aortic aneurysm repair is practiced by a wide range of physicians across varying specialties. An aortic aneurysm is an enlargement of the aorta of a patient caused by weakening in the wall of the aorta. If an aortic aneurysm is untreated, it may rupture and cause serious health complications.

The procedure for endovascular aortic aneurysm repair involves the placement of a stent graft within the aorta of a patient to seal off the aneurysm from blood flow to prevent the aneurysm from expanding. During the procedure, the diameter of the stent graft is initially reduced in order to endovascularly position the stent graft within the aorta where the aneurysm is located. After proper placement, the stent graft is deployed by removing a sheath surrounding the stent graft and releasing the mechanism that radially restrains the stent graft to a reduced diameter. The stent graft may include one or more stents positioned on the exterior of the stent graft to maintain the tubular configuration of the stent graft and to maintain the stent graft's position over the aneurysm.

In some cases, the mechanism used to initially reduce the diameter of the stent graft, or radially restrain the stent graft, included ties or wires connected to the stents of the stent graft. The ties or wires restrain the stents of the stent graft for placement of the stent graft within the aorta, and then the ties or wires are released from the stent graft during removal of the sheath surrounding the stent graft, also known as unsheathing, and allow the stent graft to expand to its unrestrained or nominal diameter.

BRIEF SUMMARY

This invention concerns systems and methods of adjusting the diameter of a stent graft that allows for controlled radial deployment of the stent graft and the ability to revise the positioning of the stent graft after unsheathing.

The present invention also relates to an endoluminal prosthesis including a stent graft having a tubular graft wall, a stent, a main strand, a proximal strand, and a distal strand. The tubular graft wall defines an internal lumen of the stent graft and has a first surface and a second surface. The stent is positioned on the first surface of the tubular graft wall and includes at least two proximal apices and at least three distal apices. The proximal strand is positioned on at least the first surface of the tubular graft wall and coupled or connected to the two proximal apices of the stent. The distal strand is positioned on at least the first surface of the tubular graft wall and connected to two of the three distal apices of the stent. The main strand is positioned along one of the first and second surfaces and connected to the proximal strand and the distal strand on one of the first and second surfaces of the tubular graft wall.

The present invention relates to a method of adjusting a diameter of an endoluminal prosthesis. The endoluminal prosthesis includes a stent graft having a tubular graft wall, a stent, a main strand, a proximal strand, and a distal strand. The method includes reducing the diameter of the endoluminal prosthesis to a second diameter via pulling the main strand distally away from the stent graft, the second diameter being smaller than the first diameter. Pulling of the main strand distally away from the stent graft also distally pulls the proximal strand that is coupled or connected to at least two proximal apices of the stent and pulls the two proximal apices toward each other, and pulling of the main strand distally away from the stent graft also distally pulls the distal strand that is connected to at least two of at least three distal apices of the stent and pulls the two distal apices toward each other. The method also includes increasing the diameter of the endoluminal prosthesis via moving the main strand proximally toward the stent graft to a third diameter, the third diameter being larger than the second diameter. The moving of the main strand proximally toward the stent graft also moves the proximal strand proximally and allows the two proximal apices to move away from each other. The moving of the main strand proximally toward the stent graft also moves the distal strand proximally and allows the two distal apices to move away from each other. The method also includes reducing the diameter of the endoluminal prosthesis via pulling the main strand distally away from the stent graft to a fourth diameter, the fourth diameter being smaller than the third diameter.

The present invention also relates to a system for adjusting a diameter of an endoluminal prosthesis. The system includes a stent graft having a tubular graft wall, a stent, a main strand, a proximal strand, and a distal strand. The tubular graft wall defines an internal lumen of the stent graft and includes a first surface and a second surface. The stent is positioned on the first surface of the tubular graft wall and includes at least two proximal apices and at least three distal apices. The proximal strand is positioned on at least the first surface of the tubular graft wall and coupled or connected to the two proximal apices of the stent. The distal strand is positioned on at least the first surface of the tubular graft wall and connected to two of the three distal apices of the stent. The main strand is positioned along one of the first and second surfaces of the tubular graft wall and connected to the proximal strand and the distal strand on one of the first and second surfaces of the tubular graft wall. The main strand includes a proximal end and a distal end, the proximal end being connected to the proximal strand and the distal end terminating in a loop. Distal movement of the distal end of the main strand reduces the diameter of the endoluminal prosthesis and proximal movement allows the endoluminal prosthesis to return to its unrestrained diameter.

The accompanying drawings, which are incorporated herein and constitute part of this specification and, together with the general description given above and the detailed description given below, serve to explain features of the present invention.

BRIEF DESCRIPTION OF THE DRAWINGS

In the drawings:

FIG. 2A shows an exploded view of the exterior surface of the endoluminal prosthesis of FIG. 1;

FIG. 2B shows an exploded view of the interior surface of the endoluminal prosthesis of FIG. 1;

FIG. 3 shows a side view of the endoluminal prosthesis of FIG. 1 in a radially restrained position;

FIG. 4 shows a side view of the endoluminal prosthesis of FIG. 1 in a radially unrestrained position;

FIG. 5 shows a side view of the endoluminal prosthesis of FIG. 1 in a radially restrained position;

FIG. 6 shows a perspective view of positioning the endoluminal prosthesis of FIG. 1 in the aorta of a patient below an aneurysm;

FIG. 7 shows a perspective view of deploying or radially unrestraining the endoluminal prosthesis of FIG. 1 in the aorta of the patient below the aneurysm;

FIG. 11 shows a side view of a second embodiment of a endoluminal prosthesis in a radially restrained position;

FIG. 12 shows a side view of the endoluminal prosthesis of FIG. 11 with portions of the endoluminal prosthesis in a radially unrestrained position and a portion of the endoluminal prosthesis in a radially restrained position;

FIG. 13 shows a side view of the endoluminal prosthesis of FIG. 11 with a radially unrestrained position;

DETAILED DESCRIPTION OF THE DRAWINGS AND THE PRESENTLY PREFERRED EMBODIMENTS

In the following detailed description of the various endoluminal prosthesis embodiments, like elements and structures are numbered or labeled alike.

Figure 1:
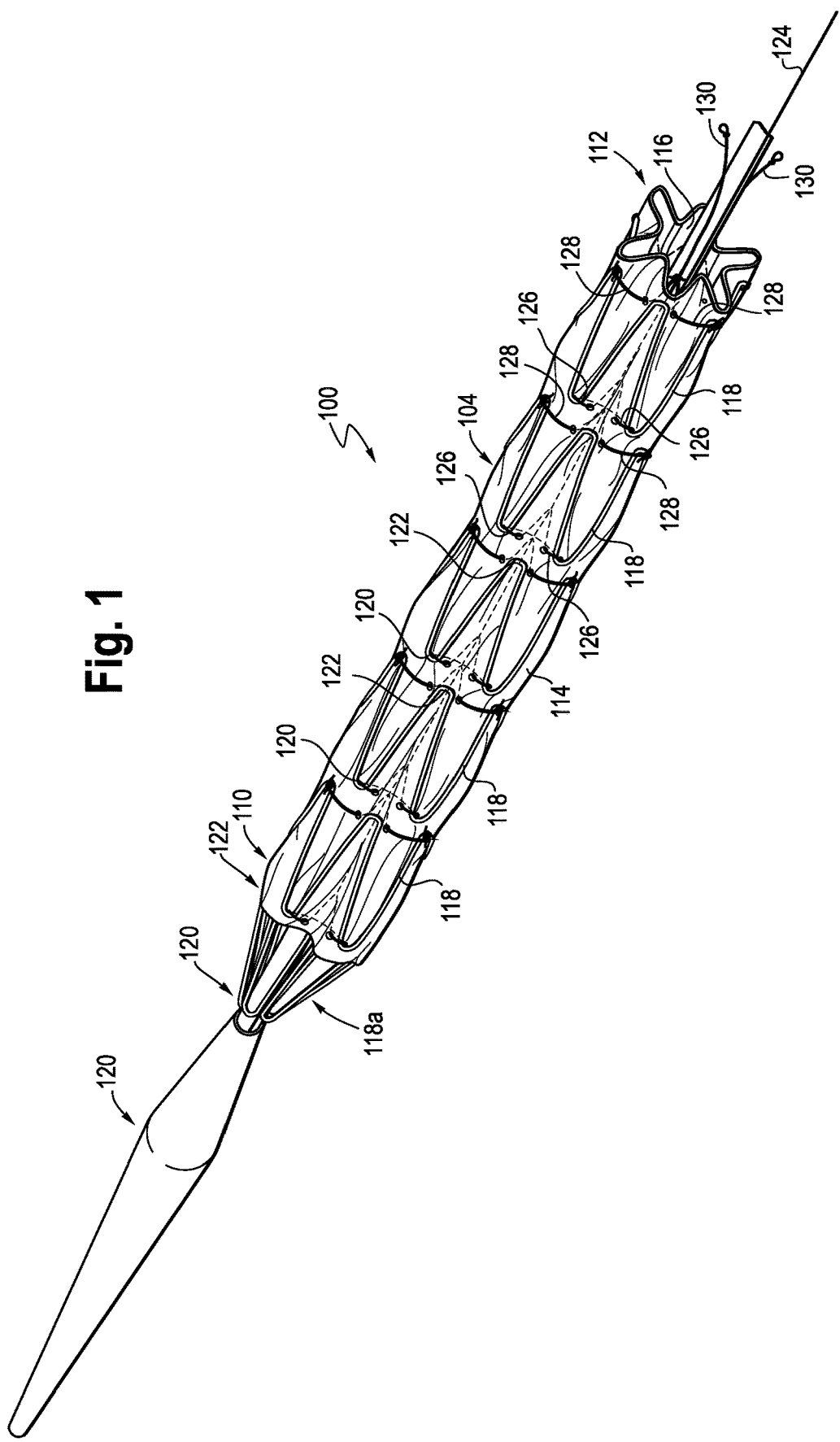
FIG. 1 shows a perspective view of an embodiment of an endoluminal prosthesis including a stent graft in a radially restrained position.
Figure 2:
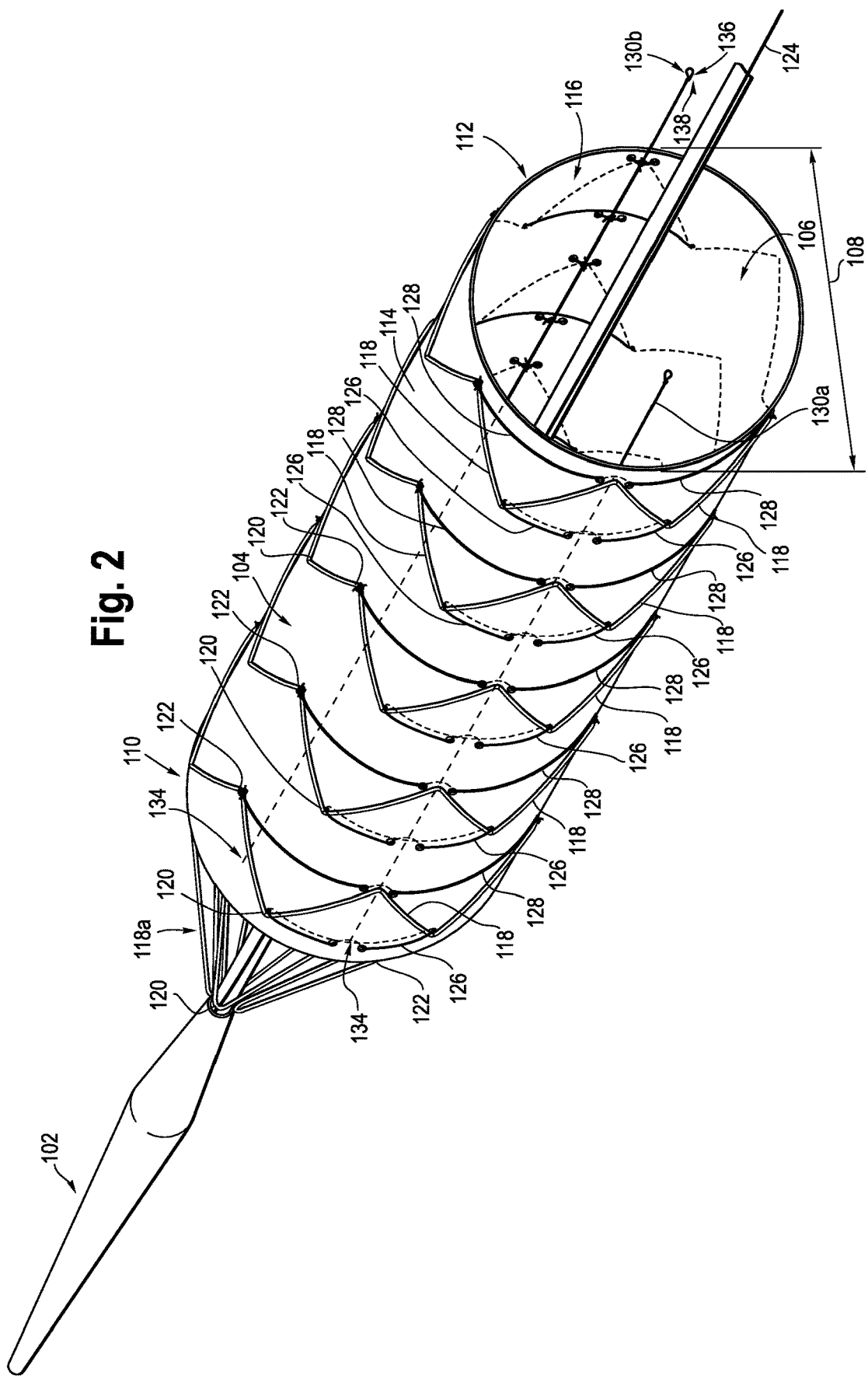
FIG. 2 shows a perspective view of the endoluminal prosthesis of FIG. 1 in a radially unrestrained position.

FIGS. 1 and 2 show an endoluminal prosthesis 100 positioned on an introducer 102 of a delivery system (not shown) in a radially restrained position and in a radially unrestrained position, respectively. Radially restrained, as used herein, relates to the endoluminal prosthesis being restrained radially and thus having any diameter smaller than its nominal diameter. The nominal diameter of the endoluminal prosthesis 100 is the maximum diameter of the endoluminal prosthesis when no radial forces are exerted on the endoluminal prosthesis 100 to reduce its diameter. Radially unrestrained, as used herein, relates to the endoluminal prosthesis being unrestrained radially either partially or fully and thus having a diameter that is the same as or smaller than its nominal diameter. The delivery system used to endovascularly implant the endoluminal prosthesis 100 into the aorta of a patient may be one known in the art.

The endoluminal prosthesis 100 includes a stent graft 104 having a tubular shape with a lumen 106 having a nominal diameter 108, a proximal end 110, a distal end 112, an abluminal, exterior or first surface 114, and a luminal, interior or second surface 116. The stent graft 104 is made of a flexible material, such as polytetrafluoroethylene (PTFE) or expanded PTFE (ePFTE), a polyester material, or other materials that allow for a seal over an aneurysm. In the present application, the term "abluminal surface" refers to the outer surface of the lumen of the stent graft 104 of the endoluminal prosthesis 100, and the term "luminal surface" refers to the inner surface of the lumen of the stent graft 104 of the endoluminal prosthesis 100.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first, and the outflow end (that end from which the fluid exits).

The endoluminal prosthesis 100 also includes a plurality of stents 118, such as Z-stents, that are connected to and positioned on the exterior surface 114 of the stent graft 104. The stents 118 are connected to the stent graft 104 via stitching, suturing, stapling or use of an adhesive. Each Z-stent may include a series of substantially straight segments or struts interconnected by a series of bent segments or bends. The bent segments may include acute bends or apices, and each Z-stent may have a plurality of proximal apices 120 and a plurality of distal apices 122. The Z-stents are arranged in a zig zag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, stents arranged on the exterior surface 114 of the stent graft 104 may have the potential to become intertwined with the wires or other devices utilized to ensure branch vessel access, sealing, and fixation. Thus, in some instances, it may be desirable to affix some of the stents to the interior surface 116 of the stent graft 104.

One of the stents 118a of the endoluminal prosthesis may be connected to the proximal end 110 of the stent graft 104 and may extend beyond the proximal end 110 of the stent graft 104, as shown in FIG. 1. The proximal apices 120 of the stent 118a are connected to the introducer 102 to form a tri-fold configuration, and the distal apices 122 of the stent 118a are connected to the proximal end 110 of the stent graft 104. The tri-fold configuration maintains the position of the stent graft 104 on the introducer 102 during implantation. A trigger wire 124 is positioned within the lumen 106 of the stent graft 104 and is connected the delivery system (not shown) for manipulation. The trigger wire 124 releases the proximal apices 120 of the stent 118a from the introducer 102 for fixation with or attachment to the aorta of the patient after stent deployment.

To control radial movement and deployment of the endoluminal prosthesis 100 during the procedure, the endoluminal prosthesis 100 includes a plurality of proximal strands 126, a plurality of distal strands 128, and one or more main strands 130 further described below. Each strand 126, 128, 130 may include a wire, such as Nitinol wire, or a monofilament thread or fiber, including a Dyneema® thread or fiber. Each stent 118 positioned on and connected to the stent graft 104 may include at least one proximal strand 126 and one distal strand 128, as shown in FIGS. 1-2.

FIGS. 2A and 2B show exploded views of the exterior surface 114 and the interior surface 116, respectively, of the stent graft 104 while the endoluminal prosthesis 100 is in a radially unrestrained position. As shown in FIGS. 2A and 2B, the proximal strand 126 and the distal strand 128 are positioned on both the exterior surface 114 and the interior surface 116 of the stent graft 104 and each are connected to the main strand 130 on the interior surface 116 of the stent graft 104. This doubling over on the exterior surface 114 and the interior surface 116 creates a pulley-type system with the main strand 130. Specifically, each proximal strand 126 and each distal strand 128 are perpendicular to the main strand 130. The stent graft 104 also may include a plurality of holes 132 for the proximal strand 126 and/or the distal strand 128 to transition from the exterior surface 114 to the interior surface 116 of the stent graft 104 and vice versa. However, the proximal 126 and the distal strand 128 may also transition from the exterior surface 114 to the interior surface 116 without the plurality of holes 132 via stitching through the stent graft 104.

The proximal strand 126 includes a first end 126a and a second end 126b that are connected to the main strand 130 via sutures, including suture loops, stitches, or other form of removable connection, as shown in FIG. 2B. Beginning with the first end 126a of the proximal strand 126, the first end 126a is connected to the main strand 130. The proximal strand 126 then extends perpendicularly from the main strand 130 and then transitions from the interior surface 116 to the exterior surface 114 through one of the plurality of holes 132 that is adjacent to the main strand 130, as shown in FIG. 2B. The proximal strand 126 then extends along the exterior surface 114 toward the nearest proximal apex 120a of the stent 118 and over one of the struts of the proximal apex 120a, as shown in FIG. 2A. The proximal strand 126 then transitions from the exterior surface 114 to the interior surface 116 through one of the plurality of holes 132 positioned adjacent and distal to the proximal apex 120a and between the struts of the proximal apex 120a to create a loop around the proximal apex 120a, such that the proximal strand 126 is coupled to the proximal apex 120a.

The proximal strand 126 then extends along the interior surface 116 toward the proximal apex 120b of the stent 118 that is adjacent to the proximal apex 120a. As shown in FIG. 2B, when the proximal strand 126 extends along the interior surface 116 to connect the proximal apex 120a to the adjacent proximal apex 120b, the proximal strand 126 extends over but does not connect with the main strand 130. The proximal strand 126 then transitions from the interior surface 116 to the exterior surface 114 through one of the plurality of holes 132 positioned adjacent and distal to the proximal apex 120b and between the struts of the proximal apex 120b to create a loop around the proximal apex 120b, such that the proximal strand 126 is coupled to the proximal apex 120b. The proximal strand 126 then extends along the exterior surface 114 toward one of the plurality of holes 132 adjacent to the proximal apex 120b, as shown in FIG. 2A, to transition from the exterior surface 114 to the interior surface 116 and then extends along the interior surface 116 toward the main strand 130. The second end 126b is then connected to the main strand 130 along the interior surface 116 of the stent graft 104, as shown in FIG. 2B.

When the main strand 130 is pulled distally, the proximal strand 126 is also pulled distally and pulls the proximal apices 120a and 120b toward each other. This movement causes the endoluminal prosthesis 100 to be radially restrained and the diameter of the stent graft 104 to be decreased from its nominal diameter 108. Also, when the main strand 130 is moved proximally or otherwise released from any distal pull movement or distal force, the proximal strand 126 is also moved proximally or released from any distal pull movement or distal force, which allows the proximal apices 120a and 120b to move away from each other toward their unrestrained position. This movement causes the stent graft 104 to expand back toward its nominal diameter 108.

As shown in FIGS. 2A and 2B, the distal strand 128 includes a first end 128a and a second end 128b, and the distal strand 128 is connected to the main strand 130, approximately at a midpoint of the length of the distal strand 128, via sutures, including suture loops, stitches, or other form of removable connection. Beginning with the first end 128a of the distal strand 128, the first end 128a of the distal strand 128 is connected to one of the distal apices 122a on the exterior surface 114 of the stent graft 104. The distal strand 128 then extends from the distal apex 122a toward the adjacent distal apex 122b. Prior to reaching the adjacent distal apex 122b, the distal strand 128 transitions from the exterior surface 114 to the interior surface 116 through one of the plurality of holes 132.

The distal strand 128 then extends toward the main strand 130 along the interior surface 116 of the stent graft 104 and is connected to the main strand 130 via sutures, including suture loops, stitches, or other form of removable connection, as shown in FIG. 2B. The distal strand 128 extends perpendicularly from the main strand 130 and then transitions from the interior surface 116 to the exterior surface 114 through one of the plurality of holes 132 adjacent to the distal apex 122b. The distal strand 128 then extends along the exterior surface 114 toward the distal apex 122c and is connected to the distal apex 122c on the exterior surface 114 of the stent graft 104 via sutures, including suture loops, stitches, or other form of removable connection. As shown in FIG. 2A, the distal strand 128 does not connect with the distal apex 122b that is positioned between the distal apices 122a and 122c.

When the main strand 130 is pulled distally, the distal strand 128 is also pulled distally and pulls the distal apices 122a and 122c toward each other and also toward the distal apex 122b. This movement causes the endoluminal prosthesis 100 to be radially restrained and the diameter of the stent graft 104 to be decreased from its nominal diameter 108. Also, when the main strand 130 is moved proximally or otherwise released from any distal pull movement or distal force, the distal strand 128 is also moved proximally or released from any distal pull movement or distal force, which allows the distal apices 122a and 122c to move away from each other and away from the distal apex 122c toward their unrestrained position. This movement causes the stent graft 104 to expand back toward its nominal diameter 108.

As shown in FIG. 2, one or more main strands 130 may be used to radially restrain the endoluminal prosthesis 100. One main strand 130 may be connected to each stent 118 of the plurality of stents 118 via each proximal strand 126 and each distal strand 128 associated with each stent 118. The distal movement of main strand 130*a* causes each proximal strand 126 and each distal strand 128 to pull the proximal apices 120*a*, 120*b* of each stent 118 toward each other and the distal apices 122*a*, 122*c* of each stent 118 toward each other and toward distal apex 122*b*. As the stents 118 extend radially around the stent graft 104 in zig zag configuration, additional main strands 130*b* and associated proximal strands 126 and distal stands 128 may be added to uniformly radially restrain the endoluminal prosthesis 100. For example, FIG. 2 shows two main strands 130*a*, 130*b*; however, any number of main strands 130 may be used to radially restrain the endoluminal prosthesis 100 uniformly or non-uniformly around its circumference.

As shown in FIG. 2, each main strand 130 includes a proximal end 134 and a distal end 136. The proximal end 134 may be connected to the proximal strand 126 adjacent to the proximal end 110 of the stent graft 104. The main strand 130 may extend from its proximal end 134 through the lumen 106 of the stent graft 104 and connect with the plurality of proximal strands 126 and the plurality of distal strands 128 within the lumen 106 of the stent graft 104, as described previously. The main strand 130 then exits out of the distal end 112 the stent graft 104. The distal end 136 of the main strand 130 terminates in a loop 138. The loop 138 is connected to an adjoining wire 140, as shown in FIGS. 6-10, that is connected to the delivery system (not shown). The delivery system actuates movement of each main strand 130 via distal and proximal movement of the adjoining wire 140. The trigger wire 124 is also used to de-couple or otherwise release each main strand 130 from the adjoining wire 140 once positioning of the endoluminal prosthesis 100 is complete.

FIGS. 3-5 show how the manipulation of the main strand 130 allows for the controlled radial movement of the endoluminal prosthesis 100. Movement of the main strand 130 in one direction, such as pulling the main strand 130 distally, i.e., towards the operator, will radially adjust the endoluminal prosthesis 100 to a smaller diameter. Such contraction can be done incrementally to various diameters. When the main strand 130 is moved in the opposite direction, i.e., proximally (away from the operator), the endoluminal prosthesis 100 can be incrementally radially expanded toward its nominal diameter 108 multiple times in a controlled manner. FIG. 3 shows the endoluminal prosthesis 100 in a radially restrained position, and FIG. 4 shows pushing proximally or otherwise releasing of the main strand 130 to move the main strand 130 proximally, which causes the endoluminal prosthesis 100 to radially expand toward its nominal diameter 108. Then, FIG. 5 shows pulling of the main strand 130 distally restrains the endoluminal prosthesis 100 and causes the diameter of the endoluminal prosthesis 100 to decrease again.

Figure 8:
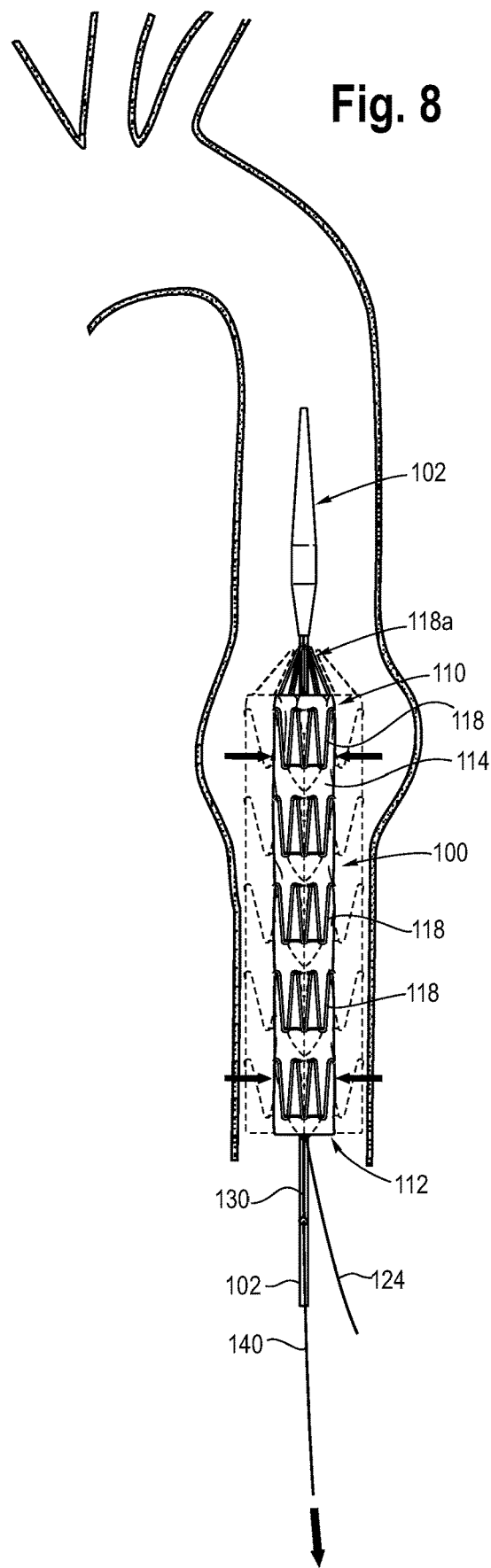
FIG. 8 shows a perspective view of radially restraining the endoluminal prosthesis of FIG. 1 after deployment.

FIGS. 6-10 show how the endoluminal prosthesis 100 may be positioned within the aorta of patient over an aneurysm. In FIG. 6, the endoluminal prosthesis 100 is positioned within, for example, an aorta of a patient via the introducer 102 of the delivery system and is in a radially restrained positioned. In this example, the endoluminal prosthesis 100 is positioned off-target and distal from the aneurysm. In this example, the endoluminal prosthesis will not properly seal off the aneurysm. In the expanded state, such as shown in FIG. 7, repositioning would be difficult or, in some cases, not possible and possibly require a further procedure to implant a second device. In FIG. 7, the wire 140 is released proximally causing the main strand 130 to move proximally, which radially expands the endoluminal prosthesis 100, and the endoluminal prosthesis 100 may expand toward its nominal diameter 108 in the off-target location distal from the aneurysm. In FIG. 8, the wire 140 is pulled distally causing the main strand 130 to move distally, which radially restrains the endoluminal prosthesis 100 back again to a diameter smaller than its nominal diameter 108.

Figure 9:
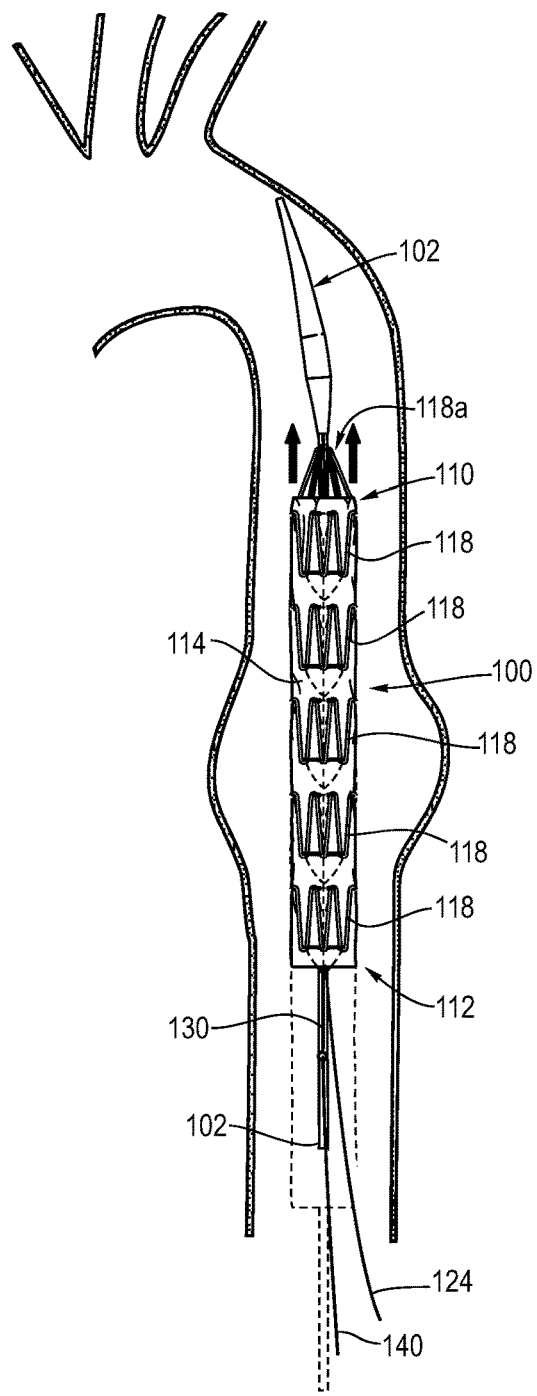
FIG. 9 shows a perspective view of repositioning the endoluminal prosthesis of FIG. 1 in a restrained position over the aneurysm.

As shown in FIG. 9, after positioning the endoluminal prosthesis 100 off-target and then reducing the diameter as described above, the introducer 102 can be moved proximally through the aorta past the aneurysm of the patient to properly position the endoluminal prosthesis 100 over the aneurysm to seal it off. During repositioning of the endoluminal prosthesis 100 in the aorta, the endoluminal prosthesis 100 should remain in the restrained position to minimize interaction of the endoluminal prosthesis 100 with the walls of the aorta of the patient. To maintain the endoluminal prosthesis 100 in a restrained position, the wire 140 and thus the main strand 130 connected to the wire 140, may be pulled distally via use of the delivery system. Once the endoluminal prosthesis 100 is properly positioned over the aneurysm, the wire 140 may be released proximally causing the main strand 130 to move proximally, which radially expands the endoluminal prosthesis 100 again toward its nominal diameter 108 in the on-target location over the aneurysm, as shown in FIG. 10.

After deployment of the endoluminal prosthesis 100 over the aneurysm, the trigger wire 124 may be used to release or de-couple the main strand 130 from the wire 140 and release or de-couple the stent 118*a* from the introducer 102. The endoluminal prosthesis 100 engages the walls the aorta to maintain its position within the aorta of the patient. The introducer 102 then moves distally through the lumen 106 of stent graft 104 and exits the aorta.

Figure 10:
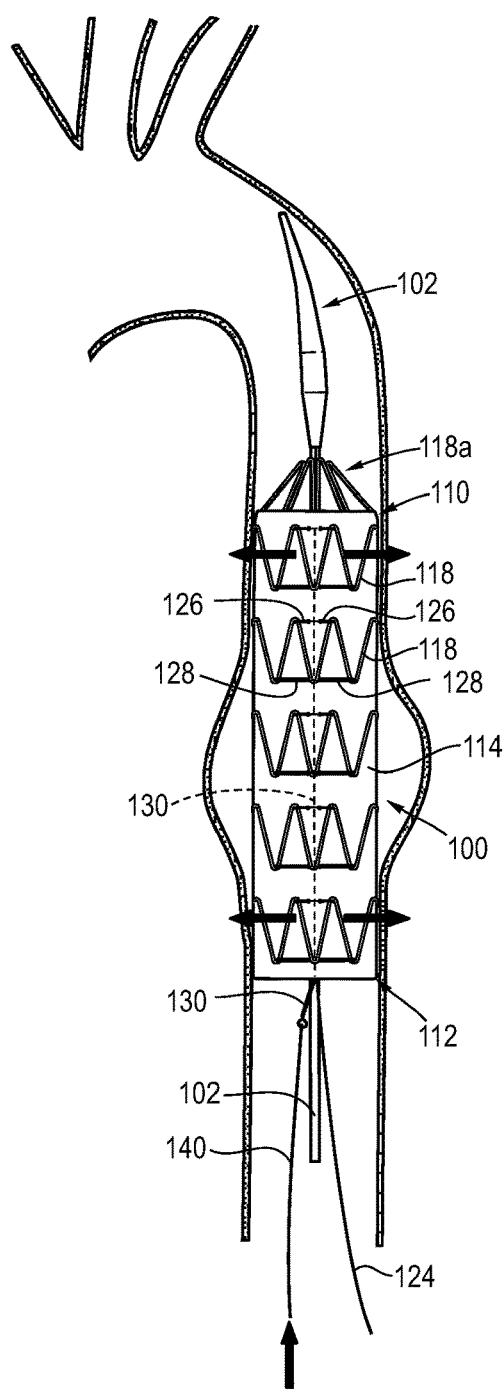
FIG. 10 shows a perspective view of deploying or radially unrestraining the endoluminal prosthesis of FIG. 1 over the aneurysm.

FIGS. 6-10 show an example of how the endoluminal prosthesis 100 may be radially restrained and radially expanded multiple times in a controlled and continuous manner. In other examples, the endoluminal prosthesis 100 may be positioned in an off-target location beyond and proximal to the aneurysm or the endoluminal prosthesis 100 may be positioned in multiple different off-target locations before being properly positioned over the aneurysm. In each off-target location, the endoluminal prosthesis 100 may be radially expanded and then radially restrained via manipulation of the main strand 130 multiple times. The main strand 130 is capable of permitting radial expansion and radial restraint until the trigger wire 124 de-couples or releases the main strand 130 from the wire 140. As shown in FIG. 10, the endoluminal prosthesis 100 has been properly placed to span the aneurysm and seal it off from blood flow.

FIGS. 11-13 show a second embodiment of an endoluminal prosthesis 100 positioned on the introducer 102 of the delivery system (not shown). In this second embodiment, one or more of the main strands 130 may be connected to only a couple of the stents 118 positioned on the stent graft 104 to allow for the manipulation of some and not all of the stents 118 on the stent graft 104 via each main strand 130.

For example, FIGS. 11-13 show two main strands 130*c*, 130*d*. Main strand 130*c* is connected to three of the five stents 118*b*, 118*e*, 118*f* positioned on the stent graft 104 via the proximal strands 126 and the distal strands 128 associated with each stent 118*b*, 118*e*, 118*f*. Main strand 130*d* is connected to the remaining two stents 118c, 118d via the proximal strands 126 and the distal strands 128 associated with each stent 118c, 118d.

In FIG. 11, both main strands 130c, 130d are pulled distally to radially restrain the endoluminal prosthesis 100 as previously described. In FIG. 12, main strain 130c is released or moved proximally, which releases stents 118b, 118e, 118f and causes them to radially expand toward the nominal diameter 108. At the same time, distal force or pulling of the main strand 130d is maintained. In this configuration, portions of endoluminal prosthesis 100 are radially restrained and the remaining portions are radially expanded toward the nominal diameter 108.

In FIG. 13, the main strand 130d is then released or moved proximally, which releases stents 118c, 118d and causes stents 118c, 118d to radially expand. FIG. 13 shows the stents 118c, 118d expanding to the same diameter as stents 118b, 118e, 118f; however, one of skill in the art will appreciate that the stents 118 may be manipulated to expand to the nominal diameter 108 of the endoluminal prosthesis 100 or to any diameter less than the nominal diameter 108 during manipulation via the main strand 130d. One of skill in the art will also appreciate that the endoluminal prosthesis 100 may include multiple main strands 130 in order to manipulate the stents 118 and the diameter of the endoluminal prosthesis 100.

Figure 14:
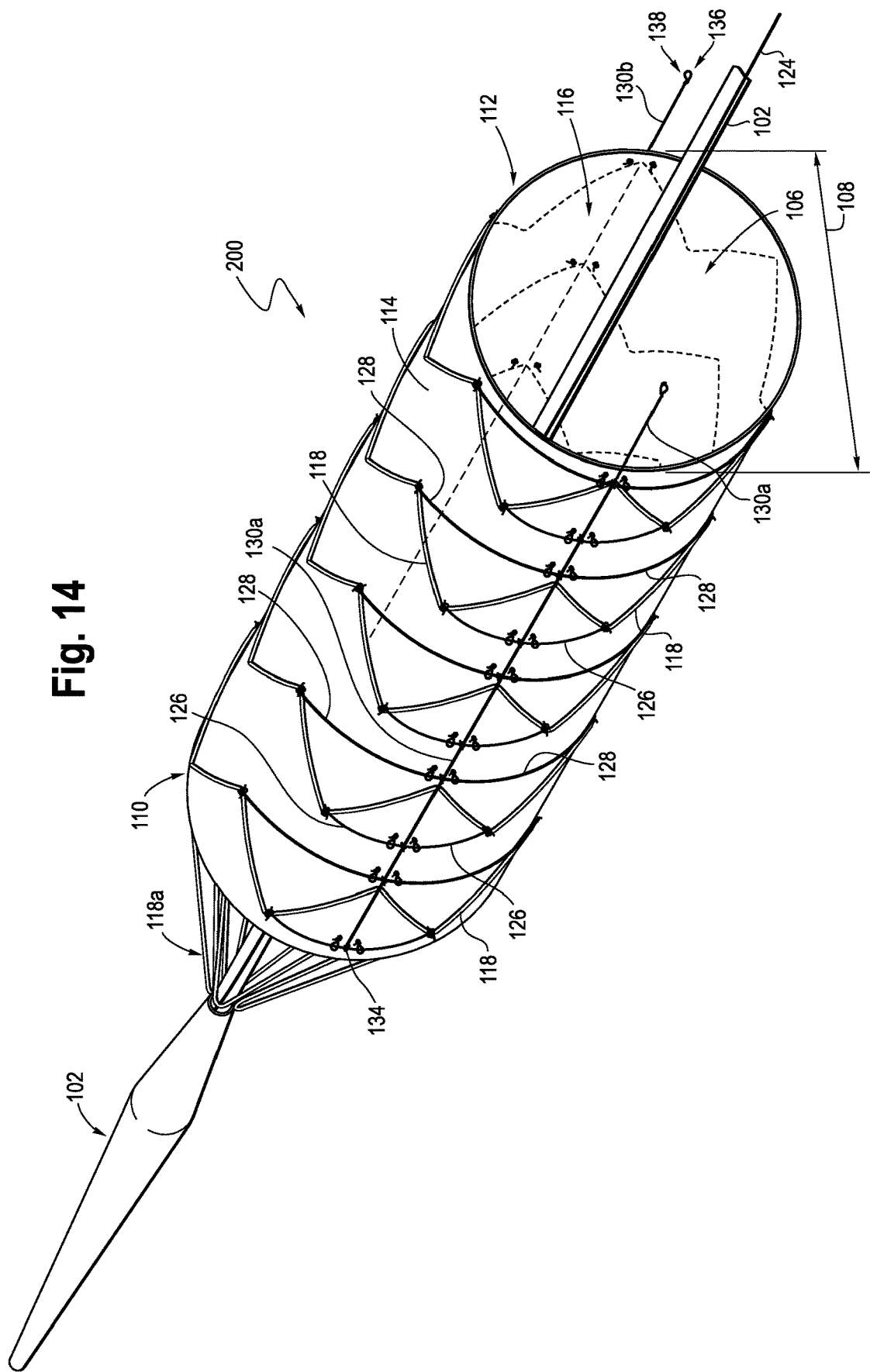
FIG. 14 shows a perspective view of another embodiment of an endoluminal prosthesis in a radially unrestrained position.
Figure 15:
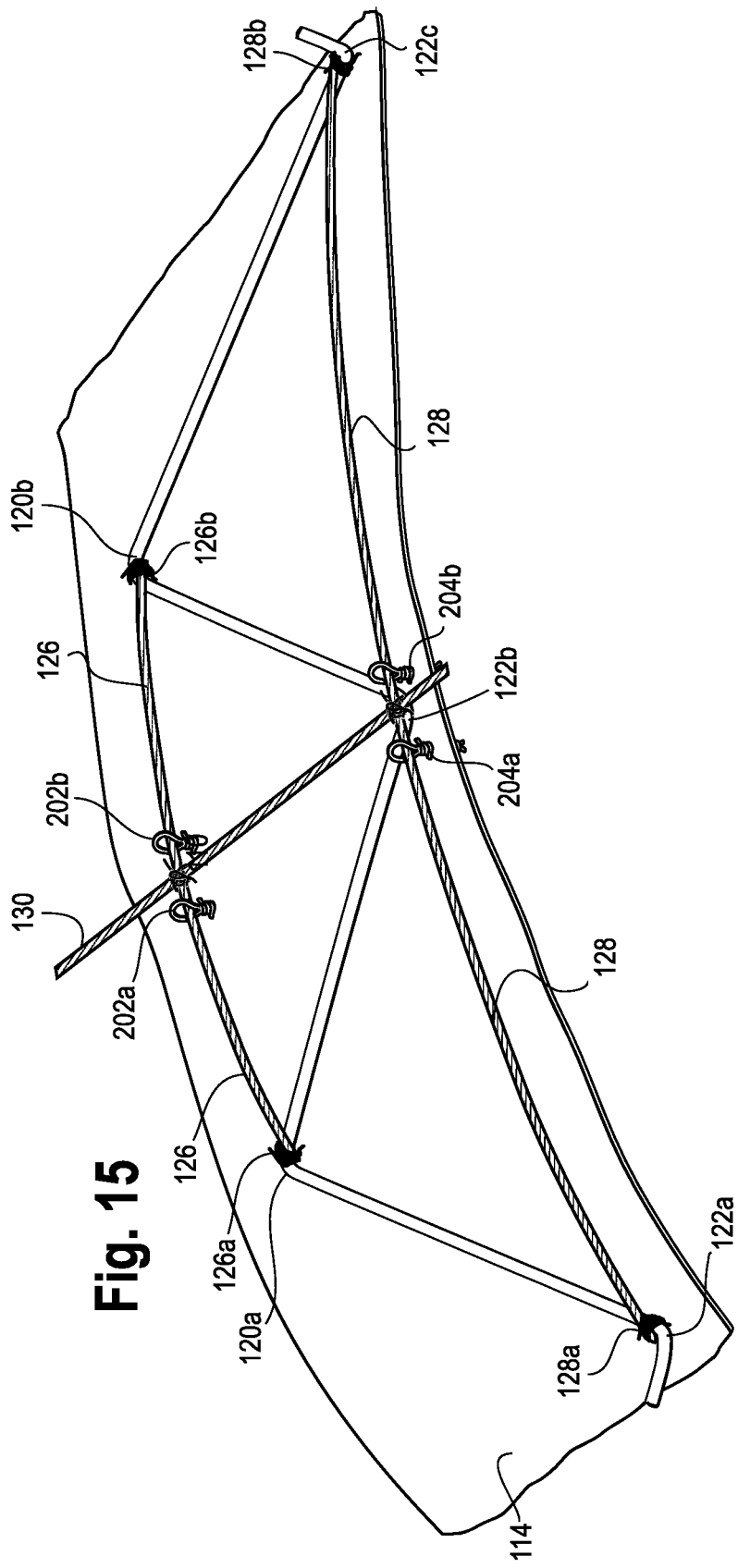
FIG. 15 shows an exploded view of the exterior surface of the endoluminal prosthesis of FIG. 14.

FIGS. 14-15 show another embodiment of an endoluminal prosthesis 200. The endoluminal prosthesis 200 includes the same features as the endoluminal prosthesis 100 except the main strands 130 are positioned on the exterior surface 114 rather than the interior surface 116 of the stent graft 104 such that the configuration of the plurality of proximal strands 126, the plurality of distal strands 128, and the main strands 130 is different. Specifically, the configuration of the plurality of proximal strands 126, the plurality of distal strands 128, and the main strands 130 is transposed. Therefore, all of the features described above regarding the endoluminal prosthesis 100 are also features of the endoluminal prosthesis 200, except for the configuration of the plurality of proximal strands 126, the plurality of distal strands 128, and the main strands 130, and are not repeated here.

FIG. 14 shows the endoluminal prosthesis 200 in an unrestrained position, and FIG. 15 shows an exploded view of the exterior surface 114 of the stent graft 104 of the endoluminal prosthesis 200. In this configuration, the proximal strand 126 and the distal strand 128 are positioned only on the exterior surface 114 and are each connected to the main strand 130 on the exterior surface 114 of the stent graft 104 to create a pulley-type system.

As shown in FIGS. 14-15, the main strand 130 is not connected to the stent 118, and the proximal and distal strands 126, 128 are only positioned on the exterior surface 114 of the stent graft 104. The first end 126a of the proximal strand 126 is connected to the proximal apex 120a of the stent 118, and the second end 126b of the proximal strand 126 is connected to the proximal apex 120b of the stent 118 that is adjacent to the proximal apex 120a. The first and second ends 126a, 126b are connected to the proximal apices 120a, 120b via sutures, including suture loops, stitches, or other form of removable connection. The proximal strand 126 extends from the proximal apex 120a along the exterior surface 114 of the stent graft 104 toward the proximal apex 120b. Prior to reaching the proximal apex 120a, the proximal strand 126 extends through a first suture loop 202a of a pair of suture loops 202 that is attached to the stent graft 104. The first suture loop 202a of the pair of the suture loops 202 is positioned on one side of the main strand 130 and the second suture loop 202b is positioned on the opposite side of the main strand. After extending through the first suture loop 202a, the proximal strand 126 intersects the main strand 130 and is connected to the main strand 130 via sutures, including suture loops, stitches, or other form of removable connection. The proximal strand 126 then extends through the second suture loop 202b and toward the proximal apex 120b. The second end 126b of the proximal strand 126 is connected to the proximal apex 120b.

The pair of suture loops 202 positioned on opposite sides of the main strand 130 allow the proximal strand 126 to slide through the suture loops 202 when the endoluminal prosthesis 200 is radially expanded and restrained and to maintain portions of the proximal strand 126 in the same plane as the proximal apices 120a, 120b of the stent 118. Specifically, when the main strand 130 is pulled distally, the proximal strand 126 is also pulled distally. In order for this action to cause the proximal apices 120a, 120b to move toward each other to radially restrain the endoluminal prosthesis 200, portions of the proximal strand 126 must be in the same plane as the proximal apices 120a, 120b to pull them together. The pair of suture loops 202 keeps portions of the proximal strand 126 within the same plane as the proximal apices 120a, 120b when the main strand 130 is pulled or released.

The first end 128a of the distal strand 128 is connected to the distal apex 122a of the stent 118 via sutures, including suture loops, stitches, or other form of removable connection. The distal strand 128 extends from the distal apex 122a toward the adjacent distal apex 122b. Prior to reaching the adjacent distal apex 122b, the distal strand extends through a first suture loop 204a of a pair of suture loops 204 that is attached to the stent graft 104. The pair of suture loops 204 is similar to the pair of suture loops 202 that the proximal strand 126 extends through. The first suture loop 204a of the pair of the suture loops 204 is positioned on one side of the main strand 130 and the second suture loop 202b is positioned on the opposite side of the main strand. After extending through the first suture loop 204a, the distal strand 128 intersects the main strand 130 and is connected to the main strand 130 via sutures, including suture loops, stitches, or other form of removable connection. The distal strand 128 is not connected to the distal apex 122b below the main strand 130. The distal strand 128 then extends through the second suture loop 204b and toward the distal apex 122c. The second end 128b of the distal strand 128 is connected to the distal apex 122c.

Similar to the pair of suture loops 202, the pair of suture loops 204 positioned on opposite sides of the main strand 130 allow the distal strand 128 to slide through the suture loops 204 when the endoluminal prosthesis 200 is radially expanded and restrained and to maintain portions of the distal strand 128 in the same plane as the distal apices 122a, 122b, 122c of the stent 118. Specifically, when the main strand 130 is pulled distally, the distal strand 128 is also pulled distally. In order for this action to cause distal apices 122a, 122c to move toward each other to radially restrain the endoluminal prosthesis 200, portions of the distal strand 128 must be in the same plane as the distal apices 122a, 122c to pull them together. The pair of suture loops 204 keeps portions of the distal strand 128 within the same plane as the distal apices 122a, 122c when the main strand 130 is pulled or released.

With this configuration, when the main strand 130 is pulled distally, the proximal and distal strand 126, 128 are also pulled distally. This action radially restrains the stent graft 104 by causing the proximal apices 120a, 120b to move toward each other and the distal apices 122a, 122c to move toward each other and also toward the distal apex 122b. To radially increase the endoluminal prosthesis 200 back toward its nominal diameter 108, the main strand 130 is released or moves proximally after being pulled. The previous steps and features described above regarding the endoluminal prosthesis 100 may also be used with the endoluminal prosthesis 200 to control radial movement and deployment of the endoluminal prosthesis 200.

The present embodiments may be used on a variety of different types of prostheses. For example, another type of endoluminal prosthesis is a bifurcated stent graft including a distal leg and a main body. The distal leg may also include a plurality of stents and each stent including a proximal strand 126 and distal strand 128 connected to the stent, and one or more main strands connected to the proximal strand 126 and the distal strand 128. The main body of the bifurcated stent graft may also include a plurality of stents and each stent including a proximal strand 126 and a distal strand 128 connected to the stent, and additional main strands 130 connected to the proximal strand 126 and the distal strand 128. Such a configuration would allow for separate and controlled radial expansion and restraining of the main body and distal leg of the bifurcated stent graft. In another example, if the stent graft 104 includes any stents 118 on the interior surface 116 of the stent graft 104, in addition to the stents 118 on the exterior surface 114, the distal and proximal strands 126, 128.

As another example, another type of endoluminal prosthesis is a stent graft that is used for insertion into a hole or opening of an existing stent graft. For example, an existing stent graft may include openings that allow for blood flow to the renal arteries after the existing stent graft is positioned within the aorta. The renal arteries may also need a stent to maintain blood flow within the renal artery. A stent graft may be implanted through the opening of the existing stent graft and into the respective renal artery. The stent graft may include a plurality of stents and each stent including a proximal strand 126 and distal strand 128 connected to the stent, and one or more main strands connected to the proximal strand 126 and the distal strand 128. The ability to manipulate the diameter of the stent graft and reposition the stent graft allows for more controlled and accurate positioning of the stent graft within the opening of the existing stent graft and the respective renal artery.

As another example, another type of endoluminal prosthesis is a stent graft that includes stents on the interior surface of the stent graft. In this example, one or more of the configurations described above with the main strands positioned on the exterior surface and/or the interior surface of the stent graft may be used.

Advantageously, the present embodiments allow for controlled and continuous radial movement of an endoluminal prosthesis. Specifically, the present embodiments control radial expansion and restraining of an endoluminal prosthesis multiple times during implantation of the endoluminal prosthesis in a patient's body. This advantage allows for more controlled, accurate and continuous deployment and implantation of an endoluminal prosthesis within the patient's body.

As another advantage, the present embodiments allow for the repositioning of an endoluminal prosthesis in a patient's body after the endoluminal prosthesis has initially been radially expanded within the patient's body. Specifically, the present embodiments permit a physician to have multiple chances to ensure accurate positioning of the endoluminal prosthesis, and also allows for more controlled and accurate implantation of an endoluminal prosthesis within the patient's body.

It will be appreciated by those skilled in the art that changes could be made to the embodiments described above without departing from the broad inventive concept therefore. It is understood, therefore, that this invention is not limited to the particular embodiments disclosed, but it is intended to cover modifications within the spirit and scope of the present invention as defined by the claims.

The invention claimed is:

1. An endoluminal prosthesis comprising:
   a stent graft comprising a tubular graft wall, a stent, a main strand, a proximal strand perpendicular to the main strand and having first and second ends, and a distal strand perpendicular to the main strand and having first and second ends;
   wherein the tubular graft wall defines an internal lumen of the stent graft and comprises a first surface and a second surface;
   wherein the stent is positioned on the first surface of the tubular graft wall and comprises at least two proximal apices and at least three distal apices;
   wherein the proximal strand is positioned on at least the first surface of the tubular graft wall with the first end connected to one of the at least two proximal apices of the stent and the second end connected to another of the at least two proximal apices of the stent;
   wherein the distal strand is positioned on at least the first surface of the tubular graft wall with the first end connected to one of the least three distal apices of the stent and the second end connected to an another of the least three distal apices of the stent;
   wherein the main strand is positioned longitudinally along one of the first and second surfaces of the tubular graft wall and connected to the proximal strand and the distal strand on one of the first and second surfaces of the tubular graft wall and moveable in at least a distal direction;
   wherein movement of the main strand in the distal direction pulls the proximal strand distally to cause the at least two proximal apices of the stent to move inwardly toward each other and reduce a diameter of the tubular graft at the at least two proximal apices of the stent.

2. The endoluminal prosthesis of claim 1, wherein the proximal strand is positioned on both of the first and second surfaces, and wherein the distal strand is positioned on both of the first and second surfaces.

3. The endoluminal prosthesis of claim 1, wherein movement of the main strand in the distal direction pulls the distal strand distally to cause at least two of the at least three distal apices of the stent to move inwardly toward each other and reduce the diameter of the tubular graft at the at least two distal apices of the stent.

4. The endoluminal prosthesis of claim 1, wherein the stent graft further comprises a second stent having at least two proximal apices and at least three distal apices, a second proximal strand having first and second ends with the first end connected to one of the at least two proximal apices of the second stent and the second end connected to another of the at least two proximal apices of the second stent, a second distal strand having first and second ends with the first end connected to one of the at least three distal apices of the second stent and a second end connected to another of the at least three distal apices of the second stent;

wherein the main strand is connected to the second proximal strand and the second distal strand on one of the first and second surfaces of the tubular graft;

wherein movement of the main strand in the distal direction pulls the second proximal strand distally to cause the at least two proximal apices of the second stent to move inwardly toward each other and reduce a diameter of the tubular graft at the at least two proximal apices of the second stent.

5. The endoluminal prosthesis of claim 4, wherein movement of the main strand in the distal direction pulls the second distal strand distally to cause the at least two of the at least three distal apices of the second stent to move inwardly toward each other and reduce a diameter of the tubular graft at the least two distal apices of the second stent.

6. The endoluminal prosthesis of claim 4, wherein the second proximal strand and the second distal strand extend through a wall of the tubular graft so that a length of both the first and second proximal strands extend over both of the first and second surfaces of the tubular graft.

7. The endoluminal prosthesis of claim 4, wherein the distal strand is a closed loop having a length that extends at least partially over an external surface of the tubular graft and a length that extends at least partially over an internal surface of the tubular graft.

8. The endoluminal prosthesis of claim 7, wherein the first end of the distal strand loops around the one of the at least three distal apices of the first stent and the second end of the distal strand loops around another of the at least three distal apices of the first stent.

9. The endoluminal prosthesis of claim 7, wherein the main strand extends along the internal surface of the tubular graft and is connected to the length of the distal strand that extends at least partially over the internal surface of the tubular graft.

10. The endoluminal prosthesis of claim 1, wherein the proximal strand is a closed loop having a length that extends at least partially over an external surface of the tubular graft and a length that extends at least partially over an internal surface of the tubular graft.

11. The endoluminal prosthesis of claim 10, wherein the first end of the proximal strand loops around the one of the at least two proximal apices of the first stent and the second end of the proximal strand loops around the other of the at least two proximal apices of the first stent.

12. The endoluminal prosthesis of claim 10, wherein the main strand extends along the internal surface of the tubular graft and is connected to the length of the proximal strand that extends at least partially over the internal surface of the tubular graft.

13. The endoluminal prosthesis of claim 1, wherein the stent graft further comprises a second stent having at least two proximal apices and at least three distal apices, a second main strand configured for proximal and distal movement independent of the main strand, a second proximal strand having first and second ends with the first end connected to one of the at least two proximal apices of the second stent and the second end connected to another of the at least two proximal apices of the second stent, a second distal strand having first and second ends with the first end connected to one of the at least three distal apices of the second stent and a second end connected to another of the at least three distal apices of the second stent;

wherein the second main strand is connected to the second proximal strand and the second distal strand on one of the first and second surfaces of the tubular graft;

wherein movement of the second main strand in the distal direction pulls the second proximal strand distally to cause the at least two proximal apices of the second stent to move inwardly toward each other and reduce a diameter of the tubular graft at the at least two proximal apices of the second stent.

14. An endoluminal prosthesis comprising:

a stent graft comprising a tubular graft wall, a stent, a main strand, a proximal strand perpendicular to the main strand and having first and second ends, and a distal strand perpendicular to the main strand and having first and second ends;

wherein the tubular graft wall defines an internal lumen of the stent graft and comprises a first surface and a second surface;

wherein the stent is positioned on the first surface of the tubular graft wall and comprises at least two proximal apices and at least three distal apices;

wherein the proximal strand is positioned on at least the first surface of the tubular graft wall with the first end connected to one of the at least two proximal apices of the stent and the second end connected to another of the at least two proximal apices of the stent;

wherein the distal strand is positioned on at least the first surface of the tubular graft wall with the first end connected to one of the least three distal apices of the stent and the second end connected to an another of the least three distal apices of the stent;

wherein the main strand is positioned longitudinally along one of the first and second surfaces of the tubular graft wall and connected to the proximal strand and the distal strand on one of the first and second surfaces of the tubular graft wall and moveable in both a distal direction and a proximal direction;

wherein movement of the main strand in the distal direction pulls the proximal strand distally to cause the at least two proximal apices of the stent to move inwardly toward each other and reduce a diameter of the tubular graft at the at least two proximal apices of the stent; and wherein movement of the main strand in the proximal direction pushes the proximal strand proximally to cause the at least two proximal apices of the stent to move outwardly away each other and increase the diameter of the tubular graft at the at least two proximal apices of the stent.

15. The endoluminal prosthesis of claim 14, wherein movement of the main strand in the distal direction pulls the distal strand distally to cause at least two of the at least three distal apices of the stent to move inwardly toward each other and reduce a diameter of the tubular graft at the at least two distal apices of the stent; and wherein movement of the main strand in the proximal direction pushes the distal strand proximally to cause the at least two distal apices of the stent to move outwardly away each other and increase the diameter of the tubular graft at the at least two distal apices of the stent.

16. The endoluminal prosthesis of claim 14, wherein the stent graft further comprises a second stent having at least two proximal apices and at least three distal apices, a second main strand configured for proximal and distal movement independent of the main strand, a second proximal strand having first and second ends with the first end connected to one of the at least two proximal apices of the second stent and the second end connected to another of the at least two proximal apices of the second stent, a second distal strand having first and second ends with the first end connected to one of the at least three distal apices of the second stent and a second end connected to another of the at least three distal apices of the second stent;

wherein the second main strand is positioned longitudinally along one of the first and second surfaces of the tubular graft wall and connected to the proximal strand and the distal strand on one of the first and second surfaces of the tubular graft wall and moveable in both a distal direction and a proximal direction independently of the main strand;

wherein movement of the second main strand in the distal direction pulls the proximal strand distally to cause the at least two proximal apices of the second stent to move inwardly toward each other and reduce a diameter of the tubular graft at the at least two proximal apices of the second stent;

wherein movement of the second main strand in the proximal direction releases the second proximal strand to cause the at least two proximal apices of the second stent to move outwardly away each other and increase the diameter of the tubular graft at the at least two proximal apices of the second stent.

17. A system for controlled radial contraction and expansion of an endoluminal prosthesis, the system comprising:

a stent graft comprising a tubular graft, a stent connected to the tubular graft, a main strand, a proximal strand, and a distal strand;

wherein the tubular graft wall defines an internal lumen of the stent graft and comprises a first surface and a second surface;

wherein the stent is positioned on the first surface of the tubular graft wall and comprises at least two proximal apices and at least three distal apices;

wherein the proximal strand is positioned on at least the first surface of the tubular graft wall and connected to the two proximal apices of the stent;

wherein the distal strand is positioned on at least the first surface of the tubular graft wall and connected to at least two of the three distal apices of the stent;

wherein the main strand is positioned along one of the first and second surfaces of the tubular graft wall and connected to the proximal strand and the distal strand on one of the first and second surfaces of the tubular graft wall and is configured to move in a proximal direction and a distal direction;

wherein the main strand comprises a proximal end connected to the proximal strand and a distal manipulation end;

wherein movement of the main strand in the distal direction reduces the diameter of the stent and an associated portion of the tubular graft and movement of the main strand in the proximal direction increases the diameter of the stent and an associated portion of the tubular graft from the reduced diameter.

18. The system of claim 17, wherein the endoluminal prosthesis further comprises a second stent, a second proximal strand, and a second distal strand;

wherein the second proximal strand is connected to at least two proximal apices of the second stent; and wherein the second distal strand is connected to at least two of three distal apices of the second stent.

19. The system of claim 18, wherein movement of the main strand in the distal direction reduces the diameter of the second stent and an associated portion of the tubular graft and movement of the main strand in the proximal direction increases the diameter of the second stent and an associated portion of the tubular graft from the reduced diameter.

20. The system of claim 17, wherein the stent graft further comprises a second stent having at least two proximal apices and at least three distal apices, a second main strand configured for proximal and distal movement independent of the main strand, a second proximal strand having first and second ends with the first end connected to one of the at least two proximal apices of the second stent and the second end connected to another of the at least two proximal apices of the second stent, a second distal strand having first and second ends with the first end connected to one of the at least three distal apices of the second stent and a second end connected to another of the at least three distal apices of the second stent;

wherein the second main strand is positioned longitudinally along one of the first and second surfaces of the tubular graft wall and connected to the proximal strand and the distal strand on one of the first and second surfaces of the tubular graft wall and moveable in both a distal direction and a proximal direction independently of the main strand;

wherein movement of the second main strand in the distal direction reduces the diameter of the stent and an associated portion of the tubular graft and movement of the second main strand in the proximal direction increases the diameter of the second stent and an associated portion of the tubular graft from the reduced diameter.

* * * * *